United States Patent [19]

Maurer

[11] Patent Number: 4,665,175
[45] Date of Patent: May 12, 1987

[54] PREPARATION OF PYRIMIDINYL PHOSPHORIC ACID DERIVATIVES AND INTERMEDIATES

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 743,454

[22] Filed: Jun. 11, 1985

[30] Foreign Application Priority Data

Jun. 27, 1984 [DE] Fed. Rep. of Germany ....... 3423622

[51] Int. Cl.$^4$ ..................... C07F 9/65; C07D 239/36; C07D 239/46
[52] U.S. Cl. .................................... 544/243; 544/298; 544/319
[58] Field of Search ............................... 544/243, 298

[56] References Cited

U.S. PATENT DOCUMENTS

| | | | |
|---|---|---|---|
| 3,249,603 | 5/1966 | Bretschneider et al. | 544/319 X |
| 3,331,841 | 7/1967 | Priewe et al. | 544/298 |
| 3,907,797 | 9/1975 | Budesinsky et al. | 544/298 |
| 4,162,310 | 7/1979 | Maurer et al. | 514/86 |
| 4,429,125 | 1/1984 | Reifschneider | 544/243 |
| 4,444,764 | 4/1984 | Reifschneider et al. | 544/298 X |
| 4,558,039 | 12/1985 | Reifschneider et al. | 544/298 X |

FOREIGN PATENT DOCUMENTS 2365577 4/1978 France .
0028776 12/1964 Japan .................................. 544/298

OTHER PUBLICATIONS

Chemical Abstracts, vol. 86, 1977, p. 440, Abstract No. 155305c.
Chesterfield et al., J. Chem. Soc., 1960, pp. 4590–4596, (1960).
McOmie et al., J. Chem. Soc., 1963, pp. 5590–5593, (1963).
Umemoto et al., Chemical Abstracts, vol. 79, 32082a, (1973).

Primary Examiner—Robert Gerstl
Assistant Examiner—Diana G. Rivers
Attorney, Agent, or Firm—Sprung Horn Kramer & Woods

[57] ABSTRACT

A process for the preparation of a compound of the formula

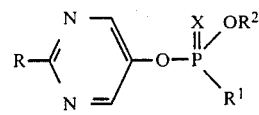

in which
R is hydrogen, alkoxy, alkylamino, dialkylamino, or optionally substituted alkyl, cycloalkyl or aryl,
$R^1$ is optionally substituted alkyl, alkoxy, alkylthio, monoalkylamino or dialkylamino, or is phenyl,
$R^2$ is optionally substituted alkyl, and
X is oxygen or sulphur, comprising reacting a compound of the formula

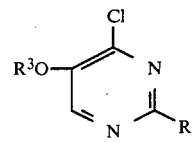

in which
$R^3$ is optionally substituted benzyl, with hydrogen in the presence of a hydrogenation catalyst, in the presence of an acid acceptor and in the presence of a diluent, at temperatures between 20° C. and 150° C., to give a compound of the formula

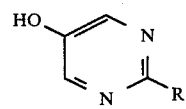

and then in a second step reacting that with a compound of the formula

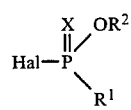

in which
Hal is halogen.

The end products are known pesticides.

8 Claims, No Drawings

PREPARATION OF PYRIMIDINYL PHOSPHORIC ACID DERIVATIVES AND INTERMEDIATES

The invention relates to a new process for the preparation of insecticidal pyrimidinyl phosphoric acid derivatives and of intermediates which can be used for carrying out the process.

It has already been disclosed that certain pesticidal pyrimidine esters of phosphoric acid are obtained when corresponding phosphoric ester chlorides are reacted with 5-hydroxypyrimidines (see U.S. Pat. No. 4,127,652, issued Nov. 28, 1978, corresponding to DE-OS (German Published Specification) No. 2,643,262 and DE-OS (German Published Specification) No. 2,706,127. However, this method of preparation has only restricted utility for this purpose because of the lack of suitable starting compounds or because of unsatisfactory methods of preparation. Thus, there is a need for new processes for the preparation of pyrimidine esters of phosphoric acid and relevant intermediates.

It has now been found that the compounds of the general formula (I)

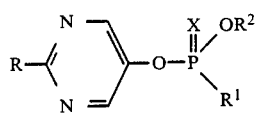

in which
R represents hydrogen, alkoxy, alkylamino, dialkylamino or optionally substituted radicals from the group comprising alkyl, cycloalkyl and aryl,
$R^1$ represents optionally substituted radicals from the group comprising alkyl, alkoxy, alkylthio, monoalkylamino or dialkylamino and phenyl,
$R^2$ represents optionally substituted alkyl, and
X represents oxygen or sulphur,
are obtained when
(a) compounds of the general formula (II)

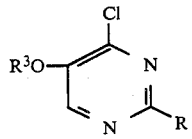

in which
R has the abovementioned meaning, and
$R^3$ represents optionally substituted benzyl,
are reacted with hydrogen in the presence of hydrogenation catalysts, in the presence of acid acceptors and in the presence of diluents, at temperatures between 20° C. and 150° C., to give the compounds of the general formula (III)

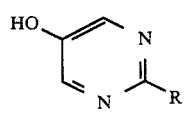

in which
R has the abovementioned meaning,
and then (b) the compounds of the general formula (III), where appropriate after their isolation, are reacted with compounds of the general formula (IV)

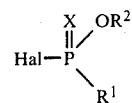

in which
Hal represents halogen, and
X, $R^1$ and $R^2$ have the abovementioned meaning,
where appropriate in the presence of an acid-binding agent and, where appropriate, in the presence of a solvent, and the compounds of the general formula (I) are isolated.

It is possible by this process to prepare the compounds of the formula (I) in a straightforward manner and in good purity and yield. The process has very wide utility in respect of the nature of the desired substituents. Furthermore, the compounds which are to be used as intermediates are stable and can easily be stored and manipulated.

Preferred substituents and ranges of the radicals detailed in the formulae mentioned above and below are illustrated by the following:

Alkoxy R represents straight-chain or branched alkoxy having, preferably, 1 to 12, in particular 1 to 6, and particularly preferably 1 to 4, carbon atoms. Examples which may be mentioned are methoxy, ethoxy, n-propoxy, i-propoxy, n-butoxy, i-butoxy, sec.-butoxy and tert.-butoxy.

Monoalkylamino or dialkylamino R represents an amino group having 1 or 2 alkyl groups, preferably 2 alkyl groups, each of which can be straight-chain or branched and which preferably contain 1 to 5, in particular 1 to 3, carbon atoms, mention being made of methyl, ethyl, n- and i-propyl. Examples which may be detailed are dimethylamino, diethylamino, di-n-propylamino and di-i-propylamino.

Optionally substituted alkyl R is represented by straight-chain or branched alkyl having 1 to 20, preferably 1 to 12, in particular 1 to 6, and particularly preferably 1 to 4, carbon atoms. Examples which may be mentioned are optionally substituted methyl, ethyl, n-propyl, i-propyl, n-butyl, sec.-butyl, i-butyl, tert.-butyl, n-pentyl, i-pentyl, and tert.-pentyl.

Optionally substituted cycloalkyl R is represented by cycloalkyl having, preferably, 3 to 8, in particular 3, 5 or 6, carbon atoms. Examples which may be mentioned are optionally substituted cyclopropyl, cyclobutyl, cyclopentyl, cyclohexyl and cycloheptyl.

Optionally substituted aryl R is represented by aryl having, preferably, 6 to 10 carbon atoms in the aryl moiety. Examples which may be mentioned are optionally substituted phenyl or naphthyl, in particular phenyl.

The substituted radicals mentioned in the definition of R can carry one or more preferably 1 to 3, in particular 1 or 2, identical or different substituents. The following substituents may be detailed for alkyl, cycloalkyl and aryl and benzyl as examples:

Alkoxy and alkylsulphonyl having 1 to 4 carbon atoms, such as methoxy, ethoxy, n-propoxy, i-propoxy, n-butoxy, i-butoxy, sec.-butoxy, tert.-butoxy, methylsulphonyl, ethylsulphonyl, n-propylsulphonyl, i-propylsulphonyl, n-butylsulphonyl, i-butylsulphonyl and tert.-butylsulphonyl.

C$_1$–C$_4$-Alkyls, such as methyl, ethyl, n-propyl, i-propyl, n-butyl, i-butyl, sec.-butyl and tert.-butyl, are also suitable as aryl substituents, cycloalkyl substituents and substituents in the phenyl ring of the benzyl group.

Preferably R represents hydrogen, alkoxy having 1 to 12 carbon atoms, monoalkylamino or dialkylamino having 1 to 6 carbon atoms in each alkyl moiety, alkyl which has 1 to 12 carbon atoms and is optionally substituted by C$_1$–C$_4$-alkoxy or C$_1$–C$_4$-alkylsulphonyl, cycloalkyl which has 3 to 8 carbon atoms and is optionally substituted by C$_1$–C$_4$-alkyl, and aryl which has 6 to 10 carbon atoms and is optionally substituted by C$_1$–C$_4$-alkyl, C$_1$–C$_4$-alkoxy or C$_1$–C$_4$-alkylsulphonyl.

Particularly preferably R represents hydrogen, alkoxy having 1 to 6 carbon atoms, monoalkylamino or dialkylamino having 1 to 4 carbon atoms in each alkyl moiety, or alkyl which has 1 to 6 carbon atoms and is optionally substituted by methoxy, ethoxy, methylsulphonyl or ethylsulphonyl, cycloalkyl which has 3 to 6 carbon atoms and is optionally substituted by methyl or ethyl, and phenyl which is optionally substituted by methyl, ethyl, methoxy, ethoxy, methylsulphonyl or ethylsulphonyl.

R very particularly preferably represents methyl, isopropyl and tert.-butyl.

The optionally substituted alkyl groups R$^1$ and R$^2$ preferably contain 1 to 6, in particular 1 to 4, and particularly preferably 1 to 2, carbon atoms. Examples which may be mentioned are methyl, ethyl, n- and i-propyl, n-, i-, s- and t-butyl.

The alkyl groups in the optionally substituted alkylamino and dialkylamino groups R$^1$ preferably have the meaning indicated above as preferable for the alkyl groups R$^1$ and R$^2$. Examples which may be detailed are methyl-, ethyl-, n- and i-propylamino and dimethyl-, di-ethyl- and methyl-ethylamino.

The alkoxy and alkylthio radicals R$^1$ preferably contain 1 to 6, in particular 1 to 4, and particularly preferably 1 or 2, carbon atoms. Examples which may be mentioned are methoxy, ethoxy, n- and i-propoxy, and methylthio, ethylthio and n- and i-propylthio.

The optionally substituted radicals R$^1$ and R$^2$ can carry one or more, preferably 1 to 3, in particular 1 or 2, identical or different substituents. Examples of substituents which may be listed are: alkyl (does not apply to the case where R$^1$ or R$^2$ represents alkyl) preferably having 1 to 4, in particular 1 or 2, carbon atoms, such as methyl, ethyl, n- and i-propyl, and n-, i-, s- and t-butyl; alkoxy preferably having 1 to 4, in particular 1 or 2, carbon atoms, such as methoxy, ethoxy, n- and i-propoxy and n-, i-, s- and t-butyloxy; alkylthio preferably having 1 to 4, in particular 1 or 2, carbon atoms, such as methylthio, ethylthio, n- and i-propylthio and n-, i-, s- and t-butylthio; halogen, preferably fluorine, chlorine, bromine and iodine, in particular chlorine and bromine; cyano and nitro.

Hal in the general formula (IV) represents fluorine, chlorine, bromine and iodine, preferably fluorine, chlorine and bromine, in particular chlorine.

The compounds of the formula (II) to be used in process step (a) are known and/or can be prepared by methods known per se, by, for example, reacting compounds of the general formula (V)

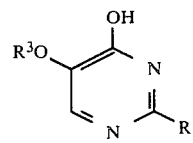

in which
R and R$^3$ have the abovementioned meanings,
in the presence of halogenating agents, such as, for example, phosphorus oxychloride, phosphorus, trichloride, oxalyl chloride, phosgene or thionyl chloride, and diluents, such as, for example, dimethylformamide or chloroform, at temperatures between 0° C. and 70° C. (see Aust. J. Chem. 29 (6), 1335 ff, J. Chem. Soc. 1960, p. 4594 and the preparation examples).

Examples of compounds of the formula (II) which can be used according to the invention and which may be listed are:

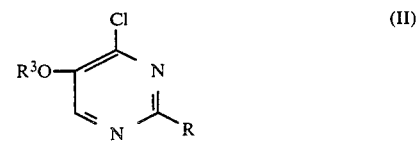

TABLE 1

| R | R$^3$ |
|---|---|
| H | CH$_2$–C$_6$H$_5$ |
| CH$_3$ | CH$_2$–C$_6$H$_5$ |
| C$_2$H$_5$ | CH$_2$–C$_6$H$_5$ |
| n-C$_3$H$_7$ | CH$_2$–C$_6$H$_5$ |
| i-C$_3$H$_7$ | CH$_2$–C$_6$H$_5$ |
| n-C$_4$H$_9$ | CH$_2$–C$_6$H$_5$ |
| i-C$_4$H$_9$ | CH$_2$–C$_6$H$_5$ |
| sec.-C$_4$H$_9$ | CH$_2$–C$_6$H$_5$ |

TABLE 1-continued

| R | R³ |
|---|---|
| tert.-C₄H₉ | CH₂—C₆H₅ |
| tert.-C₅H₁₁ (neopentyl) | CH₂—C₆H₅ |
| cyclopropyl | CH₂—C₆H₅ |
| cyclopentyl (H) | CH₂—C₆H₅ |
| cyclohexyl (H) | CH₂—C₆H₅ |
| OCH₃ | CH₂—C₆H₅ |
| OC₂H₅ | CH₂—C₆H₅ |
| OC₃H₇—n | CH₂—C₆H₅ |
| OC₃H₇—i | CH₂—C₆H₅ |
| OC₄H₉—n | CH₂—C₆H₅ |
| OC₄H₉—i | CH₂—C₆H₅ |
| OC₄H₉—sec. | CH₂—C₆H₅ |
| OC₄H₉—tert. | CH₂—C₆H₅ |
| NH₂ | CH₂—C₆H₅ |
| NH—CH₃ | CH₂—C₆H₅ |
| NH—C₂H₅ | CH₂—C₆H₅ |
| NH—C₃H₇—n | CH₂—C₆H₅ |
| NH—C₃H₇—i | CH₂—C₆H₅ |
| NH—C₄H₉—n | CH₂—C₆H₅ |
| N(CH₃)₂ | CH₂—C₆H₅ |
| N(C₂H₅)₂ | CH₂—C₆H₅ |
| N(C₃H₇—n)₂ | CH₂—C₆H₅ |
| N(C₃H₇—i)₂ | CH₂—C₆H₅ |
| N(C₄H₉—n)₂ | CH₂—C₆H₅ |
| C₆H₅— | CH₂—C₆H₅ |
| CH₃—C₆H₄— | CH₂—C₆H₅ |

TABLE 1-continued

| R | R³ |
|---|---|
| CH₃—SO₂—C₆H₄— (para) | CH₂—C₆H₅ |
| CH₃O—C₆H₄— (para) | CH₂—C₆H₅ |
| C₂H₅O—C₆H₄— (para) | CH₂—C₆H₅ |
| 3-CH₃—C₆H₄— | CH₂—C₆H₅ |
| C₂H₅—C₆H₄— (para) | CH₂—C₆H₅ |
| 2-OCH₃—C₆H₄— | CH₂—C₆H₅ |
| H | CH₂—C₆H₄—CH₃ (para) |
| CH₃ | CH₂—C₆H₄—C₂H₅ (para) |
| CH₃ | CH₂—C₆H₄—OCH₃ (ortho) |
| C₂H₅ | CH₂—C₆H₄—OC₂H₅ (para) |
| C₃H₇—i | CH₂—C₆H₄—CH₃ (ortho) |
| C₄H₉—i | CH₂—C₆H₄—OCH₃ (para) |
| C₄H₉—tert. | CH₂—C₆H₄—CH₃ (meta) |
| CH₂CH₂—OCH₃ | CH₂—C₆H₅ |
| CH₂OCH₃ | CH₂—C₆H₅ |
| CH₂CH₂—OC₂H₅ | CH₂—C₆H₅ |
| CH₂—SO₂—CH₃ | CH₂—C₆H₅ |
| CH₂—CH₂SO₂CH₃ | CH₂—C₆H₅ |

In process step (a), the compounds of the general formula (II) are converted into the compounds of the general formula (III). The process for the preparation of the compounds of the general formula (III) by process step (a) is a part of the present invention.

It has already been disclosed that 5-hydroxypyrimidines are obtained when 5-methoxypyrimidines are reacted under basic conditions in autoclaves at temperatures between 180° C. and 200° C. (see, for example, U.S. Pat. No. 4,127,652, corresponding to DE OS (German Published Specification) No. 2,643,262 and Coll. Czech. Chem. Comm. 40, 1078 ff (1975)). The disadvantages of these processes are that the yields and the purity of the reaction products are frequently unsatisfactory and, moreover, extreme reaction conditions are necessary.

It has also been disclosed that the 5-hydroxypyrimidines can also be prepared from 5-methoxypyrimidines in the presence of alkali metal hydroxides and glycol. Temperatures of about 200° C. are necessary for this process. Other disadvantages are the elaborate work-up of the final products and the moderate yields (see, for example, J. Chem. Soc. 1960, 4590 ff and Chem. Ber. 95, 803 ff (1962)). In addition, the procedure in high-boiling polar solvents such as glycol makes special efforts in waste-water purification necessary.

It has now been found that 5-hydroxypyrimidines of the formula (III)

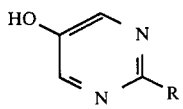

(III)

in which
R has the abovementioned meaning,
are obtained when substituted 4-chloropyrimidine derivatives of the formula (II)

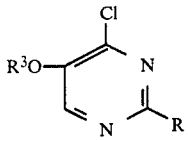

(II)

in which
R and R³ have the abovementioned meanings,
are reacted with hydrogen in the presence of hydrogenation catalysts, in the presence of acid acceptors, and in the presence of diluents, at temperatures between 20° C. and 150° C.

Surprisingly, using the process according to the invention, it is possible under relatively mild conditions to obtain the 5-hydroxypyrimidines in good yield and very high purity. Other advantages of the process are the possibility of recovery of the catalysts and the use of low-cost and more environmentally acceptable diluents.

When, for example, 5-benzyloxy-4-chloro-2-phenyl-pyrimidine, and a palladium/carbon mixture as the catalyst, are used for the process according to the invention, then the reaction can be outlined by the equation below:

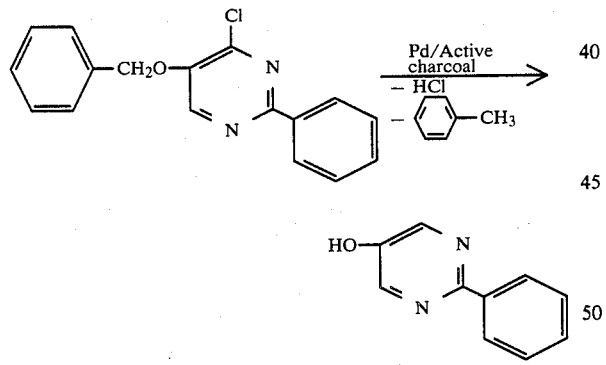

The diluents used for the preparation of the compounds of the general formula (III) from the compounds of the general formula (II) are lower aliphatic alcohols such as, for example, methanol, ethanol, n- and i-propanol, n-, i-, s- and t-butanol or two-phase systems of water and solvents which are immiscible with water, such as, for example, hexane, heptane, cyclohexane, methylcyclohexane, diethyl ether, toluene and xylene.

Suitable acid acceptors for the process according to the invention are all customarily utilisable inorganic and organic bases. These include, preferably, alkali metal carbonates, such as, for example, sodium and potassium carbonate; alkali metal hydroxides, such as, for example, sodium hydroxide; alkali metal alcoholates, such as, for example, sodium and potassium methylate and eth-ylate; and lower tertiary alkylamines, cycloalkylamines and aralkylamines, such as, in particular, triethylamine.

The process according to the invention is carried out in the presence of a hydrogenation catalyst. Neutral metal catalysts such as Raney nickel, Raney cobalt or palladium, where appropriate on customary support materials, such as, for example, active charcoal, are preferably used.

The reaction temperatures for carrying out the process according to the invention can be varied within a relatively wide range. In general, the process is carried out between 20° C. and 150° C., preferably between 20° C. and 100° C., in particular between 40° C. and 80° C.

The process according to the invention is generally carried out under elevated pressure, preferably between 5 and 60 bar, in particular between 7 and 40 bar.

To carry out the process according to the invention, between 1 and 5 moles, preferably between 1.2 and 3 moles, of acid acceptor and between 1 and 100 g, preferably between 5 and 50 g, of catalyst are used for 1 mole of 4-chloropyrimidine derivative of the formula (II).

The starting materials of the formula (II), the acid acceptor, the catalyst and the diluent are mixed and, during heating to the required temperature, hydrogen is injected. Hydrogen is injected at constant temperature until the end of the reaction is indicated by the pressure remaining constant.

Examples of the compounds of the formula (III) which may be mentioned are the following compounds:

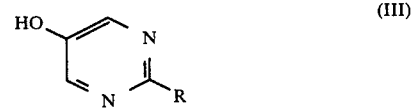

(III)

TABLE 2

| R | R |
|---|---|
| H | —CH₂CH₂OCH₃ |
| CH₃ | —CH₂OC₂H₅ |
| C₂H₅ | —CH₂CH₂OC₂H₅ |
| C₃H₇—n | —CH₂SO₂CH₃ |
| C₃H₇—i | —CH₂CH₂SO₂CH₃ |
| C₄H₉—sec. | —CH₂CH₂SO₂C₂H₅ |
| C₄H₉—tert. | —N(CH₃)₂ |
| C₅H₁₁—n | —N(C₂H₅)₂ |
| C₅H₁₁—tert. (neopentyl) | ▷— |
| OCH₃ | ⬠— |
| OC₂H₅ | ⌬H— |

| R | R | R |
|---|---|---|
| OC₃H₇—n | ⬡— | —CH₂OCH₃ |

TABLE 2-continued

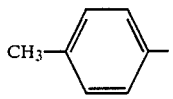

In process step (b), the compounds of the general formula (I) are obtained by reaction of the compounds of the general formulae (III) and (IV).

When, for example, O-ethyl O-isopropyl thionophosphoric chloride and 5-hydroxy-2-phenylpyrimidine are used as starting materials in process step (b), then the corresponding reaction can be outlined by the equation below:

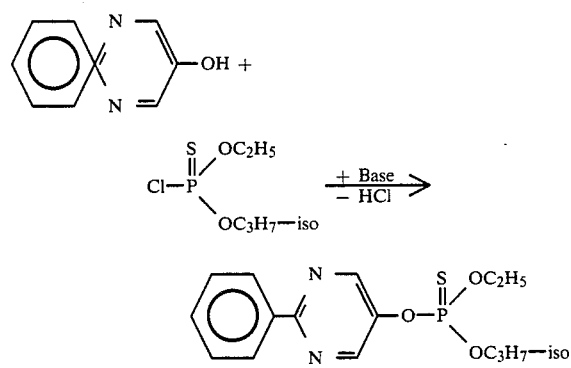

The starting materials of the general formula (IV) to be used in process step (b) are known and can readily be prepared industrially by processes and methods known from the literature. Examples of these which may be specifically mentioned are: O,O-dimethyl, O,O-diethyl, O,O-di-n-propyl, O,O-di-iso-propyl, O,O-di-n-butyl, O,O-di-iso-butyl, O,O-di-sec.-butyl, O-methyl O-ethyl, O-methyl O-n-propyl, O-methyl O-iso-propyl, O-methyl O-n-butyl, O-methyl O-iso-butyl, O-methyl O-sec.-butyl, O-ethyl O-n-propyl, O-ethyl O-iso-propyl, O-ethyl O-n-butyl, O-ethyl O-sec.-butyl, O-ethyl O-iso-butyl, O-n-propyl O-butyl and O-iso-propyl O-butyl phosphoric chloride and the corresponding thiono analogues, also O,S-dimethyl, O,S-diethyl, O,S-di-n-propyl, O,S-di-isopropyl, O,S-di-n-butyl, O,S-di-iso-butyl, O-ethyl S-n-propyl, O-ethyl S-iso-propyl, O-ethyl S-n-butyl, O-ethyl S-sec.-butyl, O-n-propyl S-ethyl, O-n-propyl S-iso-propyl, O-n-butyl S-n-propyl and O-sec.-butyl S-ethyl thiolphoshoric chloride and the corresponding thio analogues, also O-methyl, O-ethyl, O-n-propyl, O-iso-propyl, O-n-butyl, O-iso-butyl, and O-sec.-butyl methane- or ethane-, n-propane-, iso-propane-, n-butane-, iso-butane-, sec.-butane- and phenyl-phosphonic chloride and the corresponding thiono analogues, and O-methyl N-methyl, O-methyl N-ethyl, O-methyl N-n-propyl, O-methyl N-iso-propyl, O-ethyl N-methyl, O-ethyl N-ethyl, O-ethyl N-n-propyl, O-ethyl N-iso-propyl, O-n-propyl N-methyl, O-n-propyl N-ethyl, O-n-propyl N-n-propyl, O-n-propyl, N-iso-propyl, O-iso-propyl, N-methyl, O-iso-propyl N-ethyl, O-iso-propyl N-n-propyl, O-iso-propyl N-iso-propyl, O-n-butyl N-methyl, O-n-butyl N-ethyl, O-n-butyl N-n-propyl, O-n-butyl N-iso-propyl, O-iso-butyl N-methyl, O-iso-butyl N-ethyl, O-iso-butyl N-n-propyl, O-iso-butyl N-iso-propyl, O-sec.-butyl N-methyl, O-sec.-butyl N-ethyl, O-sec.-butyl N-n-propyl and O-sec.-butyl N-iso-propyl amidophosphoric chloride and the corresponding thiono analogues.

Process step (b) for the preparation of the compounds of the general formula (I) is preferably carried out with the additional use of suitable solvents and diluents. Virtually all inert organic solvents are suitable for this. These include, in particular, aliphatic and aromatic, optionally chlorinated, hydrocarbons, such as benzene, toluene, xylene, gasoline, methylene chloride, chloroform, carbon tetrachloride and chlorobenzene, or ethers, such as diethyl and dibutyl ethers and dioxane, also ketones, for example acetone, methyl ethyl, methyl isopropyl and methyl isobutyl ketones, also nitriles, such as acetonitrile and propionitrile.

All customary acid-binding agents can be used as acid acceptors. Alkali metal carbonates and alcoholates have proved particularly useful, such as sodium and potassium carbonate, and potassium tert.-butylate, also aliphatic, aromatic or heterocyclic amines, for example triethylamine, trimethylamine, dimethylaniline, dimethylbenzylamine and pyridine.

The reaction temperature can be varied within a relatively wide range. In general, the process is carried out between 0° and 100° C., preferably at 20° to 60° C.

The reaction is generally allowed to take place under atmospheric pressure.

To carry out process step (b), the equivalent ratio of the starting materials is usually employed. An excess of one or other of the components has no essential advantage. The reactants are usually mixed in one of the solvents listed above, in the presence of an acid-binding agent, and stirred for one or more hours at elevated temperature to complete the reaction. Then an organic solvent, for example toluene, is added to the mixture, and the organic phase is worked up in a customary manner by washing, drying and removing the solvent by distillation.

The compounds of the general formula (I) are usually obtained in the form of oils which frequently cannot be distilled without decomposition, but the last volatile constituents are removed by so-called "incipient distillation", that is to say by prolonged heating at moderately elevated temperatures under reduced pressure, and the compounds are purified in this manner. The refractive index serves to characterize them.

As already mentioned several times, the compounds of the general formula (I) which can be obtained according to the invention are distinguished by an excellent insecticidal, acaricidal and nematicidal action. They are active against plant, public health and store pests and in the veterinary medical sector. While their phytotoxicity is low, they have good activity against both sucking and biting insects and mites.

For this reason, the compounds of the general formula (I) which can be obtained according to the invention can be used successfully as agents to combat pests in plant protection and in the public health, store-protection and veterinary sectors.

Many of the compounds which can be obtained according to the invention and their use are known and are described in, for example, DE-OS (German Published Specification) No. 2,643,262, U.S. Pat. No. 4,127,652, European Pat. No. A 0,009,566, U.S. Pat. No. 4,325,948, U.S. Pat. No. 4,444,764 and U.S. Pat. No. 4,429,125.

As already explained above, it is possible using process steps (a) and (b) of the process according to the invention to prepare the valuable compounds of the general formula (I) in smooth reactions and in a straightforward manner, the overall yields obtained being excellent. The process (a) and (b) according to the invention surprisingly opens up, due to the specific combination of the process steps, a way to allow preparation of the compounds of the general formula (I) at a favorable cost which has not hitherto been achievable. Since the individual intermediates are stable and, especially in the case where they are isolated, they can be stored for a prolonged period, the process according to the invention also permits extremely great flexibility in production so that, if there is a sudden demand for the final products, manufacture to meet the demand is possible, and this can be of very great importance, especially due to the climate-related great seasonal variations in the plant-protection area.

In the following text, the process (and process steps) and compounds according to the invention are to be illustrated by the preparation examples which follow:

I. PROCESS FOR THE PREPARATION OF THE COMPOUNDS OF THE GENERAL FORMULA (III) (PROCESS STEP (A))

Example I/1

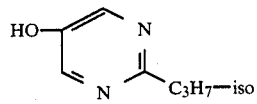

A mixture of 15.7 g (0.06 mole) of 5-benzyloxy-4-chloro-1-isopropylpyrimidine, 8.1 g (0.08 mole) of triethylamine, 1 g of 10% palladium/charcoal catalyst and 100 ml of ethanol are hydrogenated under a pressure of hydrogen of 10 bar at 50° C. After the reaction is complete, the catalyst is filtered off with suction and the filtrate is evaporated in vacuo. The residue is triturated with 25 ml of water; after crystallization, the product is filtered off with suction and washed with a little ice-water.

6 g (72% of theory) of 5-hydroxy-2-iso-propylpyrimidine are thus obtained in the form of colorless crystals with a melting point of 184° C.

EXAMPLE I/2

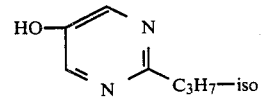

A mixture of 26.25 g (0.1 mole) of 5-benzyloxy-4-chloro-1-isopropylpyrimidine, 200 ml of methylcyclohexane and 100 ml of 2N sodium hydroxide solution is hydrogenated in the presence of 3 g of Pd/active charcoal under a pressure of hydrogen of 10 to 20 bar and at 100° C. The catalyst is then filtered off with suction, washed with a little water, and the aqueous phase of the filtrate is separated off. Adherent residues of solvent are briefly removed from the aqueous phase in vacuo and the pH is adjusted to 5 with hydrochloric acid. The precipitated product is filtered off with suction at 5° C. and washed with a little water.

In this manner, 10.8 g (78% of theory) of 5-hydroxy-2-isopropylpyrimidine are obtained in the form of colorless crystals with melting point 182° to 183° C.

In analogy to Examples I/1 and I/2, the following compounds of the formula (III)

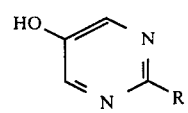

are obtained:

TABLE 3

| Example No. | R | Mp. (°C.) |
|---|---|---|
| I/3 | $C_3H_7$—n | 117 |
| I/4 | H | 216 |
| I/5 | $CH_3$ | 173 |
| I/6 | $N(CH_3)_2$ | 164 |
| I/7 | $C_2H_5$ | 149 |
| I/8 | ⟨H⟩ (cyclohexyl) | 165 |
| I/9 | phenyl | 145 |

I. (A) PREPARATION OF THE STARTING MATERIALS OF THE GENERAL FORMULA (II)

Example IA/1

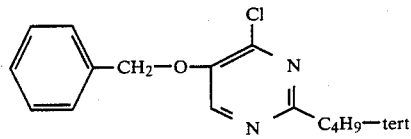

While cooling, 169 g (1.1 mole) of phosphorus oxychloride are run into a mixture of 258 g (1 mole) of 5-benzyloxy-2-tert.-butyl-4-hydroxypyrimidine and 300 ml of dimethylformamide in such a manner that the reaction temperature does not exceed 50° C. After addition is complete, the mixture is stirred for a further 3 hours without cooling, then the mixture is poured into 1 l of ice-water, and the precipitated product is filtered off with suction. It is washed with water and dried at 30° C.

257 g (93% of theory) of 5-benzyloxy-2-tert.-butyl-4-chloropyrimidine are obtained in the form of a colorless powder with melting point 51° C.

In analogy to Example (Ia/1), for example the following compounds of the formula (II) can be obtained:

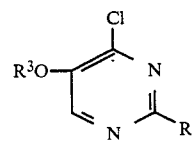

TABLE 4

| Example No. | R | R³ | Mp. (°C); Refractive index |
|---|---|---|---|
| IA/2 | C₃H₇—iso | —CH₂—C₆H₄— (benzyl) | 29 |
| IA/3 | H | —CH₂—C₆H₄— (benzyl) | 67 |
| IA/4 | C₆H₁₁ (cyclohexyl) | —CH₂—C₆H₄— (benzyl) | 112 |
| IA/5 | OCH₃ | —CH₂—C₆H₄— (benzyl) | 52 |
| IA/6 | OC₃H₇—iso | —CH₂—C₆H₄— (benzyl) | $n_D^{21}$: 1,5182 |

I. (B) PREPARATION OF THE STARTING MATERIAL OF THE GENERAL FORMULA (V)

Example IB/1

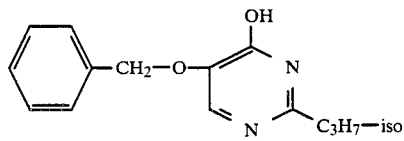

81 g (1.5 mole) of sodium methylate powder are added to a mixture of 180 g (1 mole) of methyl benzyloxyacetate and 90 g (1.5 mole) of methyl formate at a maximum of 25° C. The mixture is stirred at 20° C. for 4 hours, and then 200 ml of methanol, 0.6 mole of a methanolic solution of sodium methylate and then 122.5 g (1 mole) of isobutyramidine hydrochloride are added. During this, the reaction mixture initially cools to about 10° C. to 15° C. and then slowly warms up to about 40° C. After stirring for 16 hours, the solvent is removed by distillation in vacuo, and the residue is dissolved in about 1.5 l of water at 40° C. and, with cooling at about 30° C., sufficient concentrated hydrochloric acid is added until the pH reaches 4. The product is filtered off with suction at 5° C. and washed with water.

200 g (82% of theory) of 5-benzyloxy-4-hydroxy-2-i-propylpyrimidine are obtained as a colorless powder with melting point 198° C.

In analogy to Example IB/1, for example the following compounds of the formula (V) are prepared:

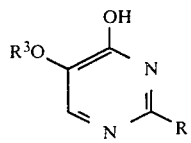

TABLE 5

| Example No. | R | R³ | Mp. (°C.) |
|---|---|---|---|
| IB/2 | C₄H₉—tert. | —CH₂—C₆H₄— (benzyl) | 155 |
| IB/3 | H | —CH₂—C₆H₄— (benzyl) | 91 |
| IB/4 | C₆H₁₁ (cyclohexyl) | —CH₂—C₆H₄— (benzyl) | 214 |
| IB/5 | OCH₃ | —CH₂—C₆H₄— (benzyl) | 165 |
| IB/6 | OC₃H₇—i | —CH₂—C₆H₄— (benzyl) | 161 |

II. PROCESS FOR THE PREPARATION OF THE COMPOUNDS OF THE GENERAL FORMULA (I) (PROCESS STEP B)

Example II/1

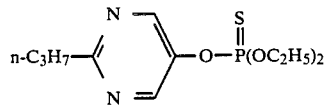

A mixture of 300 ml of acetonitrile, 13.8 g (0.1 mole) of 2-n-propyl-5-hydroxypyrimidine, 20.7 g (0.15 mole) of potassium carbonate and 18.8 g (0.1 mole) of O,O-diethyl thionophosphoric chloride is stirred at 45° C. for 2 hours. The reaction mixture is poured into 400 ml of toluene and this is washed twice with 300 ml of water each time. The toluene solution is dried over sodium sulphate and evaporated in vacuo. The residue is subjected to incipient distillation under high vacuum. 17.4 g (60% of theory) of O,O-diethyl O-[2-n-propyl-5-pyrimidinyl]thionophosphate are thus obtained in the form of a brown oil having refractive index $n^{26}$: 1.4833.

The following compounds of the formula

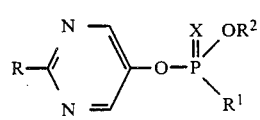

can be prepared in an analogous manner:

| Example No. | R² | R¹ | R | X | Yield (% of theory) | Refractive index |
|---|---|---|---|---|---|---|
| II/2 | C₃H₇—iso | CH₃ | C₃H₇—iso | S | 74 | $n_D^{21}$: 1.5102 |
| II/3 | CH₃ | OCH₃ | C₃H₇—iso | S | 66 | $n_D^{24}$: 1.5080 |
| II/4 | C₂H₅ | SC₃H₇—n | C₃H₇—iso | S | 69 | $n_D^{26}$: 1.5284 |
| II/5 | C₂H₅ | C₆H₅ | C₃H₇—iso | S | 74 | $n_D^{26}$: 1.5570 |
| II/6 | C₂H₅ | OC₂H₅ | C₃H₇—iso | O | 82 | $n_D^{32}$: 1.4630 |
| II/7 | C₂H₅ | NH—C₃H₇—iso | C₃H₇—iso | S | 57 | $n_D^{32}$: 1.5057 |
| II/8 | C₃H₇—n | OC₂H₅ | C₃H₇—iso | S | 73 | $n_D^{32}$: 1.4929 |
| II/9 | C₂H₅ | OC₂H₅ | CH₃ | S | 92 | $n_D^{32}$: 1.4992 |
| II/10 | C₂H₅ | C₂H₅ | CH₃ | S | 80 | $n_D^{32}$: 1.5169 |
| II/11 | C₂H₅ | OC₂H₅ | C₆H₅ | S | 80 | $n_D^{32}$: 1.5643 |
| II/12 | C₂H₅ | C₂H₅ | C₆H₅ | S | 80 | $n_D^{32}$: 1.5827 |
| II/13 | C₂H₅ | OC₂H₅ | H | S | 72 | $n_D^{32}$: 1.5028 |
| II/14 | C₂H₅ | OC₂H₅ | C₂H₅ | S | 84 | $n_D^{20}$: 1.5014 |
| II/15 | C₂H₅ | OC₂H₅ | C₄H₉—n | S | 94 | $n_D^{21}$: 1.4958 |
| II/16 | C₂H₅ | OC₂H₅ | C₄H₉—tert. | S | 86 | $n_D^{26}$: 1.4902 |

Example II/17

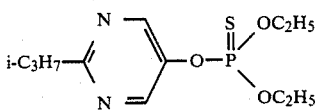

81 g (1.5 mole) of sodium methylate powder are added to a mixture of 180 g (1 mole) of methyl benzyloxyacetate and 90 g (1.5 mole) of methyl formate at a maximum of 25° C. The mixture is stirred at 20° C. for 4 hours, and then 200 ml of methanol, 0.6 mole of a methanolic solution of sodium methylate and then 122.5 g (1 mole) of isobutyramidine hydrochloride are added. During this, the reaction mixture initially cools to about 10° C. to 15° C. and then slowly warms up to about 40° C. After stirring for 16 hours, the solvent is removed by distillation in vacuo, and the residue is dissolved in about 1.5 l of water at 40° C. and, with cooling at about 30° C., sufficient concentrated hydrochloric acid is added until the pH reaches 4. The product is filtered off with suction at 5° C. and washed with water. After drying, the compound is dissolved in 600 ml of chloroform, about 50 ml of solvent is removed by distillation, and then, while boiling, 138.6 g (0.9 mole) of phosphorus oxychloride are added dropwise, and the mixture is boiled under reflux for 20 hours. After cooling to 0° C., 160 ml of concentrated ammonia solution are added dropwise, the organic phase is separated off and, after drying over sodium sulphate, the solvent is removed by distillation in vacuo.

The residue is added to a mixture of 800 ml of methyl-cyclohexane and 750 ml of 2N sodium hydroxide solution, and the mixture is hydrogenated in the presence of 15 g of Pd/active charcoal under a pressure of hydrogen of 10 to 20 bar and at 100° C. The catalyst is then filtered off with suction, washed with a little water, and the aqueous phase is removed from the filtrate. Adherent residues of solvent are briefly removed from the aqueous phase in vacuo, and the pH is adjusted to 5 with hydrochloric acid. The precipitated product is filtered off with suction at 5° C. and washed with a little water. It is dried in the air, added to a mixture of 300 ml of acetonitrile, 124.2 g (0.9 mole) of potassium carbonate and 113.1 g (0.6 mole) of O,O-diethyl thiophoshoric chloride, and the mixture is stirred at 45° C. for 2 hours. The solvent is then removed by distillation in vacuo, the residue is dissolved in 400 ml of toluene, and the solution is washed twice with 300 ml of water each time. The toluene solution is dried over sodium sulphate and evaporated in vacuo. The residue is subjected to incipient distillation under high vacuum. 170.5 g (59% of theory) of O,O-diethyl O-[2-iso-propyl-5-pyrimidinyl]thionophosphate are thus obtained in the form of a brown oil with refractive index $n_D^{21}$: 1.4970.

Example II/18

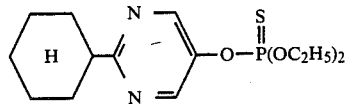

A mixture of 300 ml of acetonitrile, 17.8 g (0.1 mole) of 2-cyclohexyl-5-hydroxypyrimidine, 20.7 g (0.15 mole) of potassium carbonate and 18.8 g (0.1 mole) of O,O-diethyl thionophosphoric chloride is stirred at 45° C. for 2 hours. The reaction mixture is then poured into 400 ml of toluene and this is washed twice with 300 ml of water each time. The toluene solution is dried over sodium sulphate and evaporated in vacuo. The residue is subjected to incipient distillation under high vacuum. 21.7 g (66% of theory) of O,O-diethyl O-(2-cyclohexyl- 5-pyrimidinyl)thionophosphate are thus obtained in the form of a brown oil having refractive index $n_D^{23}$: 1.5158.

In an analogous manner, the following compounds of the formula

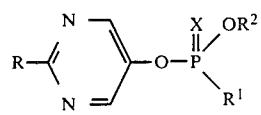

can be obtained:

| Example No. | $R^2$ | $R^1$ | R | X | Yield (% of Theory) | Physical data (refractive index: melting point °C.) |
|---|---|---|---|---|---|---|
| II/19 | $C_2H_5$ | $NH-C_3H_7-iso$ | hexagon-H | S | 51 | $n_D^{23}$: 1.5246 |
| II/20 | $CH_3$ | $OCH_3$ | hexagon-H | S | 64 | $n_D^{23}$: 1.5287 |
| II/21 | $C_2H_5$ | $OC_2H_5$ | triangle | S | 78 | $n_D^{24}$: 1.5142 |
| II/22 | $C_2H_5$ | $NH-C_3H_7-iso$ | triangle | S | 62 | 49 |
| II/23 | $CH_3$ | $OCH_3$ | triangle | S | 43 | $n_D^{24}$: 1.5390 |
| II/24 | $C_3H_7-n$ | $OC_2H_5$ | triangle | S | 71 | $n_D^{25}$: 1.5128 |
| II/25 | $C_2H_5$ | $NH-C_2H_5$ | triangle | S | 74 | $n_D^{26}$: 1.5310 |
| II/26 | $C_2H_5$ | $OC_2H_5$ | square | S | | |
| II/27 | $C_2H_5$ | $OC_2H_5$ | triangle | S | | |
| II/28 | $C_2H_5$ | $OC_2H_5$ | pentagon-H | S | 80 | $n_D^{23}$: 1.5164 |
| II/29 | $C_2H_5$ | $OC_3H_7-n$ | pentagon-H | S | | |
| II/30 | $C_2H_5$ | $CH_3$ | triangle | S | 72 | $n_D^{25}$: 1.5428 |
| II/31 | $C_2H_5$ | $OC_2H_5$ | triangle | O | | |
| II/32 | $C_2H_5$ | $NH-C_3H_7-iso$ | triangle | O | | |
| II/33 | $C_2H_5$ | phenyl | triangle | S | 74 | $n_D^{25}$: 1.5815 |

-continued

| Example No. | R² | R¹ | R | X | Yield (% of Theory) | Physical data (refractive index: melting point °C.) |
|---|---|---|---|---|---|---|
| II/34 | $C_2H_5$ | $SC_3H_7$—n | ◁ | S | | |
| II/35 | $C_2H_5$ | ⬡ | ⬠H | S | | |
| II/36 | $C_2H_5$ | NH—$C_2H_5$ | ⬠H | S | 66 | $n_D^{23}$: 1.5329 |
| II/37 | $C_2H_5$ | $SC_3H_7$ | ◁ | O | | |
| II/38 | $C_2H_5$ | $C_2H_5$ | ◁ | S | | |
| II/39 | $CH_3$ | $C_2H_5$ | ◁ | S | | |
| II/40 | $C_3H_7$—iso | $CH_3$ | ◁ | S | 67 | $n_D^{26}$: 1.5233 |
| II/41 | $CH_3$ | NH—$C_3H_7$—iso | ◁ | S | | |
| II/42 | $CH_3$ | NH—$CH_3$ | ◁ | S | 66 | $n_D^{26}$: 1.5460 |
| II/43 | $C_2H_5$ | NH—$CH_3$ | ◁ | S | | |
| II/44 | $CH_3$ | NH—$C_2H_5$ | ◁ | S | | |
| II/45 | $C_2H_5$ | NH—$C_3H_7$—iso | ⬠H | S | 55 | $n_D^{23}$: 1.5247 |
| II/46 | $C_2H_5$ | $OC_2H_5$ | ◁$CH_3$ | S | | |

Example II/47

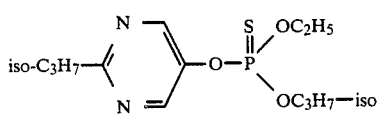

A mixture of 300 ml of acetonitrile, 13.8 g (0.1 mole) of 5-hydroxy-2-iso-propylpyrimidine, 20.7 g (0.15 mole) of potassium carbonate and 20.2 g (0.1 mole) of O-ethyl O-iso-propyl thionophosphoric chloride is stirred at 45° C. for 2 hours. The reaction mixture is then poured into 400 ml of toluene and this is washed twice with 300 ml of water each time. The toluene solution is dried over sodium sulphate and evaporated in vacuo. The residue is subjected to incipient distillation under high vacuum.

28 g (92% of theory) of O-ethyl O-iso-propyl O-(2-iso-propyl-5-pyrimidinyl)thionophosphate are thus obtained in the form of a yellow oil having refractive index $n^{23}$: 1.4910.

In an analogous manner, the following compounds of the formula

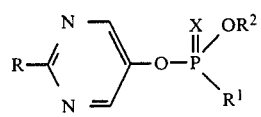

(I)

can be prepared:

| Example No. | R | $R^2$ | $R^1$ | Refractive index |
|---|---|---|---|---|
| II/48 | —$C_3H_7$—iso | —$C_3H_7$—iso | —$OC_3H_7$—iso | $n_D^{20}$: 1.4869 |
| II/49 | —$C_4H_9$—tert. | —$C_2H_5$ | —$OC_3H_7$—iso | $n_D^{20}$: 1.4917 |
| II/50 | —$C_3H_7$—iso | —$C_2H_5$ | —$OC_4H_9$—sec. | $n_D^{20}$: 1.4960 |
| II/51 | —$C_4H_9$—tert. | —$C_2H_5$ | —$OC_4H_9$—sec. | $n_D^{22}$: 1.4935 |
| II/52 | —$C_4H_9$—tert. | —$C_3H_7$—iso | —$OC_3H_7$—iso | $n_D^{22}$: 1.4857 |
| II/53 | 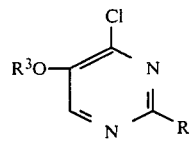 | —$C_2H_5$ | —$OC_3H_7$—iso | $n_D^{22}$: 1.5516 |
| II/54 | —$C_4H_9$—tert. | —$C_2H_5$ | —$NHC_2H_5$ | $n_D^{21}$: 1.5100 |
| II/55 | 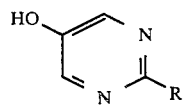 | —$C_2H_5$ | —$OC_4H_9$—sec. | |
| II/56 | 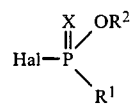 | —$C_3H_7$—iso | —$OC_3H_7$—iso | |
| II/57 | —$C_3H_7$—iso | —$C_3H_7$—n | —$OC_3H_7$—n | $n_D^{23}$: 1.4915 |

It will be understood that the specification and examples are illustrative but not limitative of the present invention and that other embodiments within the spirit and scope of the invention will suggest themselves to those skilled in the art.

What is claimed is:

1. A process for the preparation of a compound of the formula

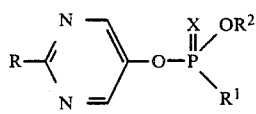

in which

R is hydrogen, alkoxy having 1 to 12 carbon atoms, monoalkylamino or dialkylamino having 1 to 6 carbon atoms in each alkyl moiety, alkyl which has 1 to 12 carbon atoms and is optionally substituted by $C_1$-$C_4$-alkoxy or $C_1$-$C_4$ alkylsulphonyl, cycloalkyl which has 3 to 8 carbon atoms and is optionally substituted by $C_1$-$C_4$-alkyl, or aryl which has 6 to 10 carbon atoms and is optionally substituted by $C_1$-$C_4$-alkyl, $C_1$-$C_4$-alkoxy or $C_1$-$C_4$-alkylsulphonyl, $R^1$ is $C_1$ to $C_6$-alkyl optionally substituted with $C_1$ to $C_4$-alkoxy, $C_1$ to $C_4$-alkylthio, halogen, cyano or nitro; $C_1$ to $C_6$-alkoxy optionally substituted with $C_1$ to $C_4$-alkyl, $C_1$ to $C_4$-alkoxy, $C_1$ to $C_4$-alkylthio, halogen, cyano or nitro; $C_1$ to $C_6$-alkylthio optionally substituted with $C_1$ to $C_4$-alkyl, $C_1$ to $C_4$-alkoxy, $C_1$ to $C_4$-alkylthio, halogen, cyano or nitro, or alkylamino or dialkylamino having 1 to 6 carbon atoms in each alkyl moiety and optionally substituted with $C_1$ to $C_4$-alkyl, $C_1$ to $C_4$-alkoxy, $C_1$ to $C_4$-alkylthio, halogen, cyano or nitro, $R^2$ is $C_1$ to $C_6$-alkyl optionally substituted with $C_1$ to $C_4$-alkoxy, $C_1$ to $C_4$-alkylthio, halogen, cyano or nitro, and X is oxygen or sulphur, comprising reacting a compound of the formula

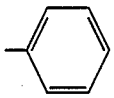

in which $R^3$ is benzyl, with hydrogen in the presence of a hydrogenation catalyst, in the presence of an acid acceptor and in the presence of a diluent, at temperatures between 20° C. and 150° C., to give a compound of the formula

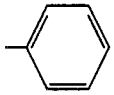

and then in a second step reacting that with a compound of the formula

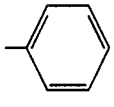

in which

Hal is halogen.

2. A process according to claim 1, wherein the second step is effected in the presence of an acid-binding agent and in the presence of a solvent.

3. A process according to claim 1, in which
R is $C_1$-$C_4$-alkyl, $C_3$-$C_6$-cycloalkyl or phenyl,
$R^1$ is $C_1$-$C_4$-alkoxy,
$R^2$ is $C_1$-$C_4$-alkyl, and
X is sulphur.

4. A process according to claim 1, in which
R is $C_1$-$C_4$-alkyl,
$R^1$ is $C_1$-$C_4$-alkoxy,
$R^2$ is $C_1$-$C_4$-alkyl, and
X is sulphur.

5. A process for the preparation of a 5-hydroxypyrimidine of the formula

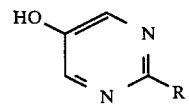

in which

R is hydrogen, alkoxy having 1 to 12 carbon atoms, monoalkylamino or dialkylamino having 1 to 6 carbon atoms in each alkyl moiety, alkyl which has 1 to 12 carbon atoms and is optionally substituted by $C_1$-$C_4$-alkoxy or $C_1$-$C_4$-alkylsulphonyl, cycloalkyl which has 3 to 8 carbon atoms and is optionally substituted by $C_1$-$C_4$-alkyl, or aryl which has 6 to 10 carbon atoms and is optionally substituted by $C_1$-$C_4$-alkyl, $C_1$-$C_4$-alkoxy or $C_1$-$C_4$-alkylsulphonyl, which comprises reacting a substituted 4-chloropyrimidine derivative of the formula

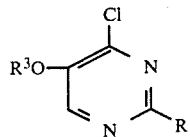

in which $R^3$ is benzyl, with hydrogen in the presence of a hydrogenation catalyst, in the presence of an acid acceptor and in the presence of a diluent, at a temperature between 20° C. and 150° C.

6. A process according to claim 5, in which
R is hydrogen, alkoxy having 1 to 6 carbon atoms, monoalkylamino or dialkylamino having 1 to 4 carbon atoms in each alkyl moiety, alkyl which has 1 to 6 carbon atoms and is optionally substituted by methoxy, ethoxy, methylsulphonyl or ethylsulphonyl, cycloalkyl which has 3 to 6 carbon atoms and is optionally substituted by methyl or ethyl, or phenyl which is optionally substituted by methyl, ethyl, methoxy, ethoxy, methylsulphonyl or ethylsulphonyl.

7. A process according to claim 5, in which R is $C_1$-$C_4$-alkyl, $C_3$-$C_6$-cycloalkyl or phenyl.

8. A process according to claim 5, in which R is methyl, ethyl, isopropyl, or t.-butyl.

* * * * *